US012754190B2

(12) United States Patent
Zhang et al.

(10) Patent No.: US 12,754,190 B2
(45) Date of Patent: Oct. 6, 2026

(54) OCCULT BLOOD DETECTION FILM, AND PREPARATION METHOD THEREFOR AND USE THEREOF AND OCCULT BLOOD DETECTION KIT

(71) Applicants: Ankon Medical Technologies (Shanghai) Co., LTD., Shanghai (CN); ANX IP HOLDING PTE. LTD., Singapore (SG)

(72) Inventors: Shupeng Zhang, Shanghai (CN); Xiaodong Duan, Pleasanton, CA (US)

(73) Assignees: ANKON MEDICAL TECHNOLOGIES (SHANGHAI) CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 927 days.

(21) Appl. No.: 18/017,855

(22) PCT Filed: Jul. 23, 2021

(86) PCT No.: PCT/CN2021/108224
§ 371 (c)(1),
(2) Date: Jan. 24, 2023

(87) PCT Pub. No.: WO2022/017512
PCT Pub. Date: Jan. 27, 2022

(65) Prior Publication Data

US 2023/0273225 A1 Aug. 31, 2023

(30) Foreign Application Priority Data

Jul. 24, 2020 (CN) ........................ 202010725944.0

(51) Int. Cl.
*G01N 33/72* (2006.01)
*C08J 5/18* (2006.01)
(Continued)

(52) U.S. Cl.
CPC .............. *G01N 33/721* (2013.01); *C08J 5/18* (2013.01); *C08J 7/065* (2013.01); *G01N 21/78* (2013.01);
(Continued)

(58) Field of Classification Search
CPC ................ G01N 33/721; G01N 21/78; G01N 2021/7759; C08J 5/18; C08J 7/065;
(Continued)

(56) References Cited

U.S. PATENT DOCUMENTS

2013/0202499 A1 8/2013 Gil et al.

FOREIGN PATENT DOCUMENTS

CN 103113606 A 5/2013
CN 104327294 A 2/2015
(Continued)

OTHER PUBLICATIONS

Guo, Jiangna. Synthesis and characterization of Imidazolium-type Poly(ionic liquid)-based functionalized members. China Doctoral Dissertations Full-text Database; Engineering Science and Technology I , No. 2016/08, Aug. 15, 2016. p. 12 paragraph3, pp. 13-14 sections 2.2.2.1-2.2.2.2.
(Continued)

*Primary Examiner* — Dennis White
(74) *Attorney, Agent, or Firm* — Treasure IP Group, LLC

(57) ABSTRACT

The present application provides an occult blood detection film, a preparation method therefor, a use thereof and an occult blood detection kit. The preparation method for the occult blood detection film comprises the following steps: providing a polyionic film; immersing the polyionic film into a dye solution, so that the dye is attached to the polyionic film to obtain the occult blood detection film, where the dye is suitable for reacting with hemoglobin, the colors of the dye are different in environments with different
(Continued)

hemoglobin concentrations, and the dye comprises at least one of a methylene blue dye or a procyanidin dye. The present application has the characteristics of easy operation, strong anti-interference performance, obvious color change, high detection speed, etc., and can alleviate the problems of high technical requirements, high cost and complicated detection.

14 Claims, 1 Drawing Sheet

(51) Int. Cl.
*C08J 7/06* (2006.01)
*G01N 21/78* (2006.01)

(52) U.S. Cl.
CPC ........ *C08J 2333/20* (2013.01); *C08J 2339/06* (2013.01)

(58) Field of Classification Search
CPC ................ C08J 2333/20; C08J 2339/06; C08J 2339/04; C08J 7/00; C08F 220/48; C08F 226/06
See application file for complete search history.

(56) References Cited

FOREIGN PATENT DOCUMENTS

| | | | | |
|---|---|---|---|---|
| CN | 111202528 A | * | 5/2020 | ......... A61B 5/14546 |
| CN | 111227843 A | | 6/2020 | |
| WO | 2019171409 A1 | | 9/2019 | |

OTHER PUBLICATIONS

Sun, J. et al. Identification of procyanidin a2 as polyphenol oxidase substrate in pericarp tissues of litchi fruit. Journal of Food Biochemistry, vol. 31, No. 3, Jun. 6, 2007, ISSN: 1745-4514. abstract.

* cited by examiner

| Hemoglobin concentration (ug/ml) | Hue (H) | Saturation (S) | Intensity (I) | Red (R) | Green (G) | Blue (B) |
|---|---|---|---|---|---|---|
| 140 | 38 | 90 | 44 | 112 | 75 | 11 |
| 28 | 46 | 77 | 56 | 143 | 117 | 33 |
| 14 | 47 | 61 | 58 | 148 | 128 | 64 |
| 7 | 51 | 56 | 58 | 147 | 134 | 64 |
| 3.5 | 55 | 60 | 52 | 133 | 127 | 53 |
| 0.7 | 51 | 14 | 56 | 143 | 140 | 123 |
| 0 | 57 | 18 | 48 | 123 | 122 | 101 |

OCCULT BLOOD DETECTION FILM, AND PREPARATION METHOD THEREFOR AND USE THEREOF AND OCCULT BLOOD DETECTION KIT

CROSS-REFERENCE OF RELATED APPLICATIONS

The application is a National Phase Application of PCT International Application No. PCT/CN2021/108224, International Filing Date Jul. 23, 2021, published Jan. 27, 2022 as International Publication Number WO2022/017512A1, which claims priority from Chinese Patent Application No. 202010725944.0, filed Jul. 24, 2020, all of which are incorporated herein by reference in their entirety.

FIELD OF INVENTION

The present application relates to the field of occult blood detection, and more particularly to an occult blood detection film, a preparation method therefor, an application thereof and an occult blood detection kit.

BACKGROUND

Clinically, for chronic bleeding, minor bleeding or bleeding under tumor conditions, occult blood detection of the gastric juice, vomit or feces of a patient is usually required for determination. Occult blood is "latent bleeding", which means that the presence of red blood cells cannot be observed with naked eyes or microscope, that is, bleeding that cannot be confirmed with naked eyes or microscope. Occult blood examination is of great value in the diagnosis of various gastrointestinal bleeding diseases, and is an effective means for general screening of gastrointestinal diseases.

At present, the common test methods of fecal occult blood mainly include chemical method and immunological method. Among them, there are many kinds of chemical methods, including chemical chromogenic method, phenolphthalein method, pyramidon method, leuco malachite green method, tetramethylbenzidine method, etc. The principle of these chemical chromogenic methods is basically the same, that is, fecal occult blood contains hemoglobin produced after the rupture of blood cells, and the porphyrin structure in hemoglobin has the activity similar to peroxidase. In the presence of hemoglobin, peroxide can be catalyzed to generate very active nascent oxygen, which has very strong oxidizing ability and can color reducing substances such as guaiac, benzidine, phenolphthalein, pyramidon, leuco malachite green or tetramethylbenzidine. According to the color development result, it can be determined whether there is occult blood in feces. In addition, the depth of color reflects the amount of hemoglobin, that is, the amount of bleeding.

In the prior art, some researches have been carried out on test methods for occult blood detection, but the existing occult blood detection still has more or less defects, for example, some existing methods for detecting fecal occult blood by using fecal occult blood test strip have the defects of high technical requirements, high cost or relatively complicated detection, and need to be further improved.

SUMMARY OF THE INVENTION

An object of the present application is to provide an occult blood detection film, a preparation method therefor, an application thereof and an occult blood detection kit, which have the advantages of simple operation, strong anti-interference performance, obvious color change, rapid detection, etc., and can overcome the above problems or at least partially solve the above technical problems.

In order to achieve the object, the technical solution adopted by the present application is as follows.

According to one aspect of the present application, the present application provides a preparation method for an occult blood detection film, comprising the following steps:

- providing a polyionic film;
- immersing the polyionic film in a dye solution and making a dye attached to the polyionic film to obtain an occult blood detection film;
- where the dye reacts with hemoglobin, and the color of the dye is different in environments with different hemoglobin concentrations;
- the dye comprises at least one of a methylene blue dye or a procyanidin dye.

In one possible embodiment, the concentration of the dye in the dye solution is 0.5-5 mg/mL, preferably 1-2 mg/mL.

Preferably, the time for immersing the polyionic film in the dye solution is 20-40 min, preferably 25-30 min, and the temperature for immersing the polyionic film in the dye solution is 20-40° C., preferably 25-35° C.

In one possible embodiment, the preparation method for the polyionic film comprises the following steps:

- providing a base plate assembly comprising a base plate and a first lubricant disposed on the base plate;
- placing a film-forming solution of the polyionic film on the base plate assembly, and putting a cover plate with a second lubricant on the film-forming solution, where the film-forming solution is in contact with the first lubricant and the second lubricant, respectively; and
- separating the polyionic film from the base plate assembly and the cover plate after a polymerization reaction of various raw materials in the film-forming solution to obtain the polyionic film.

Preferably, the base plate assembly further comprises a tinfoil, where the tinfoil is arranged on the base plate, and the first lubricant is arranged on the tinfoil.

In one possible embodiment, the first lubricant and the second lubricant are each independently selected from at least one of white petrolatum, silicone oil, paraffin, mineral oil, or grease.

In one possible embodiment, the polymerization reaction is carried out under irradiation of ultraviolet light;

- where the wavelength of the ultraviolet light is preferably 250-400 nm;
- the irradiation time of ultraviolet light is preferably 10-30 min.

In one possible embodiment, the method of separating the polyionic film from the base plate assembly and the cover plate comprises:

- removing the base plate assembly, placing the cover plate attached with the polyionic film in a standing solution, standing for 10-30 min, and removing the cover plate to obtain the polyionic film;
- or, removing the cover plate, placing the base plate assembly attached with the polyionic film in a standing solution, standing for 10-30 min, and removing the base plate assembly to obtain the polyionic film.

Preferably, removing the base plate, placing the cover plate attached with the polyionic film and the tinfoil in a standing solution, standing for 10-30 min, and removing the tinfoil to obtain the polyionic film.

Preferably, after separating the polyionic film from the base plate assembly and the cover plate, the method further comprises the step of cleaning the polyionic film, comprising ultrasonic cleaning in clear water, an alcohol solution and clear water in sequence.

In one possible embodiment, the preparation method for the film-forming solution comprises:

uniformly mixing an ionic liquid monomer and a base film monomer, adding a cross-linking agent and an initiator, and then carrying out a second ultrasonic treatment to obtain the film-forming solution.

Preferably, the time of the second ultrasonic treatment is 10-30 min.

Preferably, the preparation method for the film-forming solution further comprises performing a first ultrasonic treatment on the ionic liquid monomer, where the first ultrasonic treatment lasts for 10-30 min.

Preferably, the film-forming solution comprises at least one of an imidazole ionic liquid, a pyridine ionic liquid, a quaternary ammonium salt ionic liquid, a quaternary phosphine ionic liquid or a pyrrolidine ionic liquid.

Preferably, the ionic liquid monomer comprises bromobutane and vinylimidazole; preferably, a molar ratio of bromobutane to vinylimidazole is 2:1 to 1:1.

Preferably, the base film monomer comprises acrylonitrile; Preferably, the mass of the acrylonitrile is greater than or equal to the sum of the mass of the bromobutane and the vinylimidazole.

Preferably, the cross-linking agent comprises N,N'-methanediylbisprop-2-enamide; preferably, the mass of the cross-linking agent is 8 wt %-12 wt % of the total mass of the bromobutane, the vinylimidazole and the acrylonitrile.

Preferably, the initiator comprises 2,4,6-(trimethylbenzoyl) diphenyl phosphine oxide; preferably, the mass of the initiator is 1 wt %-4 wt % of the total mass of the bromobutane, the vinylimidazole and the acrylonitrile.

According to another aspect of the present application, there is provided an occult blood detection film comprising:

a polyionic film; and a dye attached to the polyionic film.

The occult blood detection film can be prepared by the preparation method for the occult blood detection film.

In one possible embodiment, the dye is suitable for reacting with hemoglobin, and the color of the dye is different in environments with different hemoglobin concentrations.

In one possible embodiment, the dye comprises at least one of a methylene blue dye or a procyanidin dye.

In one possible embodiment, the raw material of the polyionic film comprises an ionic liquid, and the ionic liquid comprises at least one of an imidazole ionic liquid, a pyridine ionic liquid, a quaternary ammonium salt ionic liquid, a quaternary phosphine ionic liquid or a pyrrolidine ionic liquid.

Preferably, the ionic liquid monomer for forming the polyionic film comprises bromobutane and vinyl imidazole.

Preferably, the base film monomer for forming the polyionic film comprises acrylonitrile.

Preferably, the cross-linking agent for forming the polyionic film comprises N,N'-methanediylbisprop-2-enamide.

Preferably, the initiator for forming the polyionic film comprises 2,4,6-(trimethylbenzoyl) diphenyl phosphine oxide.

According to another aspect of the present application, an application of the above-mentioned occult blood detection film or a detection film prepared by the above-mentioned preparation method for the occult blood detection film in occult blood detection is provided, and the application method comprises:

contacting the occult blood detection film with a sample to be detected, wherein the dye in the occult blood detection film reacts with hemoglobin, and the color of the occult blood detection film changes.

In a possible embodiment, the detection method further comprises: determining the concentration of the hemoglobin according to the different colors shown by the occult blood detection film, where the occult blood detection film has different colors in environments with different hemoglobin concentrations.

According to another aspect of the present application, further an occult blood detection kit is provided, which comprises the occult blood detection film or a detection film prepared by the preparation method for the occult blood detection film.

In a possible embodiment, the occult blood detection kit further comprises a standard colorimetric card for occult blood detection.

Compared with the prior art, the technical solution provided by the present application can achieve the following beneficial effects.

The occult blood detection film provided by the present application comprises a polyionic film and a dye attached to the polyionic film, where the polyionic film and the dye can have a good coordination, the dye can change color, and the dye can be used for reacting or interacting with hemoglobin in occult blood. Therefore, when the occult blood detection film is used for occult blood detection, the detection effect can be achieved without intermediate substances such as nascent oxygen, and the hemoglobin concentration can be determined by observing the change degree of the occult blood detection film before and after detection. For example, the hemoglobin concentration can be determined by observing the change of color depth (tone) of the film before and after detection, so that the occult blood detection film can be used for detecting the occult blood condition of the digestive tract, so as to assist in examination and corresponding treatment.

The present application has the advantages of simple and convenient operation, strong anti-interference performance, obvious changes before and after detection, fast detection, high efficiency, etc.

The preparation method for the occult blood detection film of the present application, comprises the steps of providing the polyionic film, immersing the polyionic film into the dye, and attaching the dye to the polyionic film; and the preparation method has the advantages of simplicity and convenience in synthesis, sensitivity in detection, easiness in operation, low technical threshold, easiness in realizing large-scale production and the like, and therefore has great application potential.

It should be understood that the above general description and the details to be set forth in the following text are only exemplary, which are not intended to limit the present application.

BRIEF DESCRIPTION OF THE DRAWINGS

In order to more clearly illustrate the embodiments of the present application or the technical solutions in the prior art, the following briefly introduces the accompanying drawings that need to be used in the description of the embodiments or the prior art.

DETAILED DESCRIPTION

Figures 1, 2:
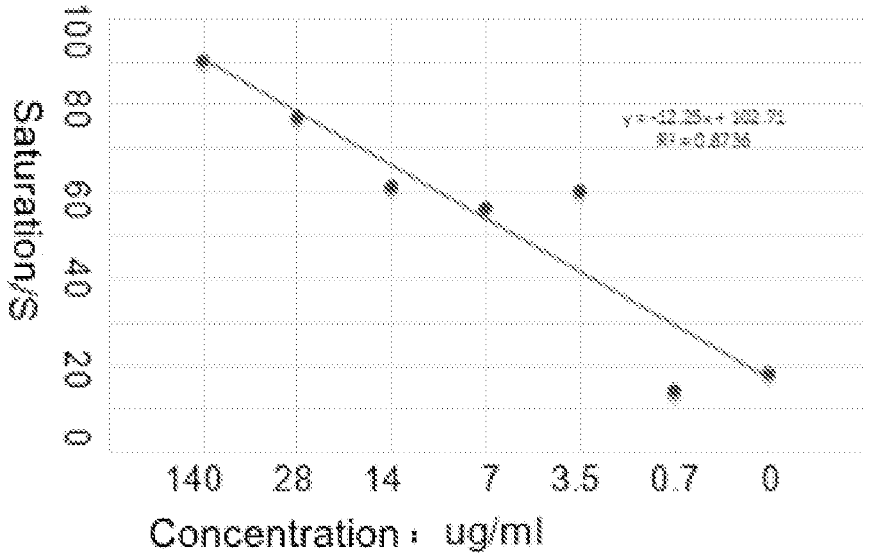
FIG. 1 is a schematic view showing a relationship between the concentration and saturation S value of hemoglobin according to an embodiment of the present application.
FIG. 2 is a contrast relationship table of concentration of hemoglobin and color of film according to an embodiment of the present application.

In order to make the object, technical solution and advantages of the present application more clear, the technical solution of the present application will be clearly and completely described below in combination with the embodiments of the present application. Obviously, the described embodiments are a part of the embodiments of the present application, rather than all the embodiments. All other embodiments obtained by those skilled in the art without creative work based on the technical solutions and embodiments provided in the present application belong to the protection scope of the present application. The embodiments in which specific conditions are not indicated are carried out under conventional conditions or conditions suggested by the manufacturer.

It should be noted that the term "and/or" or the "/" used herein only means an association relationship describing associated objects, indicating that there can be three types of relationships. For example, A and/or B can refer to: only A exists, both A and B exist, and only B exists. The singular forms "a", "said" and "the" used in the embodiments of the present application and the appended claims are also intended to include plural forms, unless the context clearly indicates other meanings.

The endpoints of ranges and any values disclosed herein are not limited to the precise ranges or values, and such ranges or values should be understood to include values approaching such ranges or values. For numerical ranges, between endpoints of individual ranges, between endpoints or individual point values of individual ranges, and between individual point values may be combined with each other to yield one or more new numerical ranges.

All the technical features and preferred features mentioned herein can be combined with each other to form new technical solutions unless otherwise specified. Unless otherwise defined or indicated, technical and scientific terms used herein have the same meaning as is familiar to those skilled in the art.

Those skilled in the art understand that, as mentioned in the background, the existing occult blood detection methods or the instruments and equipment used therein have the disadvantages of high technical difficulty, complex structure or equipment, complex test, high cost, and inability to meet the current large-scale requirements, and still need to be improved. For example, the prior art provides a fecal occult blood detection test strip, which comprises a color developing layer capable of generating color change with hemoglobin and latex arranged on a test strip body for sealing the periphery of the color developing layer. Although the method is simple, the test strip is susceptible to external interference and has high requirements on storage conditions. For example, the test strip cannot develop color after being immersed in water or wet, and the test strip is relatively toxic, so there is a certain carcinogenic possibility, which affects the use. For another example, the prior art provides a colloidal gold duplex test strip for detecting fecal occult blood and a preparation method thereof, which is composed of a substrate and a sample pad, a marking pad, a coating film and absorbent paper which are jointed and pasted on the substrate in sequence, wherein the marking pad contains a mouse anti-human Hb monoclonal antibody Hb1 and a mouse anti-human Tf monoclonal antibody Tf1 labeled with colloidal gold. The method can be used for synchronously detecting hemoglobin and transferrin in feces, has strong specificity and sensitivity, and obviously improves the positive detection rate of gastrointestinal hemorrhagic diseases. However, although this method is sensitive, it has high technical requirements, high cost and is complicated in detection.

Therefore, in order to overcome the imperfections of the prior art and further meet a large number of current requirements, the technical solutions of the embodiments of the present application provide an occult blood detection film, a preparation method therefor, an application thereof, and an occult blood detection kit, so as to achieve the effects of simple operation, low technical threshold, high detection efficiency, short preparation period, simplicity in preparation, easiness in operation, low cost, easiness in large-scale production and use, etc.

In a first aspect, in some embodiments there is provided an occult blood detection film, comprising:

a polyionic film; and a dye attached to the polyionic film.

In the occult blood detection film, the polyionic film can be a polyionic liquid type film, which has the excellent performances of an ionic liquid and a polymer, can overcome the fluidity of the ionic liquid, has unique physical and chemical properties, and can be well applied to the field of medical detection, such as the field of digestive tract detection.

In the occult blood detection film, the dye is a compound which has a certain color and can enable other substances to obtain bright or obvious color. In the embodiments of the present application, the dye can change color, and the dye and the polyionic film can form good stable coordination. Specifically, the polyionic film can adsorb the dye, or the dye can be well attached to the polyionic film, and the dye can be well maintained on the polyionic film due to strong ionic interaction between the polyionic film and the dye.

Compared with the prior art, the embodiments of the present application use direct catalytic oxidation of the dye on the hemoglobin for color development, which has the advantages of simple operation, strong anti-interference performance, obvious color change, fast detection, etc.

Specifically, the specific shape of the occult blood detection film may be of various types. For example, it may be any shape such as a circle, a square, a polygon or other irregular shapes, or it may be a sheet, a strip, etc. The embodiments of the present application do not limit the specific shape of the occult blood detection film.

Specifically, the size of the occult blood detection film can also be adjusted according to actual conditions, for example, according to the concentration of the dye solution. The embodiments of the present application do not limit the specific size of the occult blood detection film.

There is a certain correlation between the size of the occult blood detection film, such as area size, thickness, and the concentration of the dye solution. In general, the detection effect of the occult blood detection film is better in a certain size range at a certain concentration of dye solution. For example, when the concentration of dye in the dye solution is 2 mg/mL, the (area) size of the occult blood detection film may be 100-1000 $mm^2$, typically but not limiting, for example, may be 100 $mm^2$, 200 $mm^2$, 300 $mm^2$, 400 $mm^2$, 500 $mm^2$, 600 $mm^2$, 1000 $mm^2$, etc. When the concentration of dye in the dye solution is 4 mg/mL, the (area) size of the occult blood detection film may be 500-1000 $mm^2$, typically but not limiting, for example, may be 500 $mm^2$, 600 $mm^2$, 700 $mm^2$, 800 $mm^2$, 900 $mm^2$, 1000 $mm^2$, etc. When the concentration of dye in the dye solution is 0.5 mg/mL, the (area) size of the occult blood detection film may be 50-200 $mm^2$, typically but not limiting, for example, may be 50 $mm^2$, 80 $mm^2$, 100 $mm^2$, 150 $mm^2$, 200 $mm^2$, etc.

In some embodiments, the dye is suitable for reacting with hemoglobin, and the color of the dye is different in an environment with different hemoglobin concentrations. That is, the dye has a different color when the hemoglobin concentration is different. Therefore, color is developed by the direct catalytic oxidation of the dye to hemoglobin, and the detection result can be obtained by observing the color change of the occult blood detection film. It can be understood that the depth of color development reflects the concentration of hemoglobin, that is, it can reflect the amount of bleeding, and whether there is occult blood and the degree of occult blood can be determined according to the concentration of hemoglobin.

In some embodiments, the dye includes, but is not limited to, at least one of a methylene blue dye or a procyanidin dye. Where, the methylene blue dye is a non-toxic dye, which generally presents blue in an oxidized form, and can be colorless in a reduced form. Procyanidins are a class of polyphenolic compounds synthesized through the secondary metabolic pathway of plant flavonoids, which have extremely strong antioxidant activity. Such compounds from different sources have certain differences in appearance and color, and are safe and nontoxic.

It should be noted that the dye can be a methylene blue dye, or a procyanidin dye, or a mixed dye of the methylene blue dye and the procyanidin dye, but is not limited thereto. More generally, the dye may be any dye meeting the following three conditions: (1) can be stably combined with a polyionic film; (2) can specifically react with blood or substances in blood such as hemoglobin; (3) meet the requirements of biological safety.

Specifically, in the occult blood detection film, in one aspect, the polyionic film can be a carrier or platform of the dye, and the dye can be well maintained or attached to the polyionic film due to strong ionic interaction between the polyionic film and the dye, especially the methylene blue dye and/or the procyanidin dye, that is, the dye can be stably combined with the polyionic film. In another aspect, the dyes, especially the methylene blue dye and/or the procyanidin dye, are biological stains and have catalytic oxidation effect on hemoglobin. In the reaction process, the color of the methylene blue dye and/or the procyanidin dye can change after being reduced by hemoglobin. For example, it can change from blue to light yellow, and the depth (tone) of color change is different according to different hemoglobin concentrations, so that the occult blood can be quantitatively detected through color change.

As can be seen from the above, the embodiments of the present application directly use dyes such as the methylene blue dye and/or the procyanidin dye to produce corresponding changes in the chemical reaction or chemical change of hemoglobin, so as to achieve the detection effect, and the hemoglobin concentration can be determined according to the color change degree before and after detection. For example, the hemoglobin concentration in a liquid environment can be determined according to the change of color shade (tone), so as to assist in examination and corresponding treatment. The occult blood detection film can be used for measuring the hemoglobin concentration of different organs or parts. For example, the occult blood of the stomach, the intestinal tract and other organs can be measured, and the occult blood detection film has the characteristics of simple operation, obvious color change, fast detection, high efficiency, low requirements on detection personnel, etc.

In some embodiments, the raw material of the polyionic film comprises an ionic liquid, and the ionic liquid comprises, but is not limited to, at least one of an imidazole ionic liquid, a pyridine ionic liquid, a quaternary ammonium salt ionic liquid, a quaternary phosphine ionic liquid or a pyrrolidine ionic liquid. It can be understood that, according to the function of the ionic liquid, the ionic liquid used for preparing the polyionic film may be a functionalized ionic liquid commonly used in the art. Exemplarily, the ionic liquid may be an imidazole ionic liquid, a pyridine ionic liquid, a quaternary ammonium salt ionic liquid, or a pyrrolidine ionic liquid. The embodiments of the present application are not limited to the specific type of the ionic liquid, and the ionic liquids listed above can be used, and other types of ionic liquids known in the art can also be used.

Preferably, the ionic liquid monomer for forming the polyionic film comprises bromobutane and vinylimidazole. It can be understood that bromobutane and vinylimidazole can react and form ionic liquid monomers.

Preferably, the base film monomer for forming the polyionic film includes, but is not limited to, acrylonitrile. The base film monomer may be acrylonitrile, or a mixture of acrylonitrile and styrene, or other base film monomers commonly used in the art with similar functions or effects.

Preferably, the cross-linking agent for forming the polyionic film includes, but is not limited to, N,N'-methanediylbisprop-2-enamide (MBA for short). The MBA used as a cross-linking agent plays a bridging role among molecular monomers. Molecules are mutually bonded and cross-linked into a net structure, promoting the bonding among polymer molecular chains. In addition, the cross-linking agent may also be other cross-linking agents with similar properties or functions commonly used in the art.

Preferably, the initiator for forming the polyionic film includes, but is not limited to, 2,4,6-(trimethylbenzoyl) diphenyl phosphine oxide (TPO for short). The TPO is a photoinitiator, which is a light yellow solid and is mainly used for photocuring. The initiator is a high-efficiency universal ultraviolet photoinitiator and can be used to initiate the UV polymerization reactions of unsaturated prepolymer system. In addition, the initiator can also be other initiators with similar properties or functions commonly used in the art. For example, the initiator may be an initiator commonly used in the art, such as photoinitiator 907, photoinitiator 184, azobisisobutyronitrile, benzoin and derivatives thereof. Those skilled in the art can select an appropriate initiator depending on the specific type of the ionic liquid monomer, the base film monomer, etc.

It should be noted that the embodiments of the present application are not limited to the specific type of the ionic liquid, the specific type of the base film monomer, the specific type of the cross-linking agent and the specific type of the initiator, and various types commonly used in the art can be used as long as the object of the present application is not limited. For the convenience of description, the embodiments of the present application mainly take MBA as a cross-linking agent, TPO as an initiator, acrylonitrile as a base film monomer, and an ionic liquid monomer formed by bromobutane and vinylimidazole as an example to specifically describe the occult blood detection film and the preparation method thereof. However, those skilled in the art can appreciate that the principles disclosed herein may be implemented in any suitable polyionic film raw material. Further, descriptions of well-known functions or actions may be omitted for clarity and conciseness.

In a second aspect, in some embodiments, there is provided a preparation method for an occult blood detection film, comprising the steps of:

providing a polyionic film;

immersing the polyionic film in a dye and making the dye attached to the polyionic film to obtain an occult blood detection film.

Where the dye is suitable for reacting with hemoglobin, and the color of the dye is different in environments with different hemoglobin concentrations. The dye comprises at least one of a methylene blue dye or a procyanidin dye.

The preparation method for the occult blood detection film is a simple, convenient and efficient preparation method, and has the advantages of simplicity and convenience in synthesis, easiness in operation, low technical threshold, easiness in realizing large-scale production and the like.

It should be understood that, for the same or similar parts in the preparation method for the occult blood detection film according to the second aspect and the occult blood detection film according to the first aspect, the description of the preparation method for the occult blood detection film of the first aspect can be a reference, and is not described here.

In some embodiments, the concentration of the dye in the dye solution is 0.5-5 mg/mL, preferably 1-2 mg/mL; typically but not limiting, for example, may be 0.5 mg/mL, 1 mg/mL, 1.5 mg/mL, 2 mg/mL, 2.5 mg/mL, 3 mg/mL, 4 mg/mL, 5 mg/mL, etc. The dye with proper concentration range can make the final display effect better, which is more beneficial to accurately detect the concentration of hemoglobin.

Alternatively, the solvent of the dye solution may be water or an alcohol solvent, for example, may be a lower alcohol, and further may be an alcohol solvent such as ethyl alcohol. That is, the methylene blue dye or the procyanidin dye may be dissolved in water or in an alcoholic solvent.

In some embodiments, the polyionic film is immersed in the dye solution for a period of 20-40 min, preferably 25-30 min; typically but not limiting, for example, may be 20 min, 25 min, 30 min, 40 min, etc. The temperature at which the polyionic film is immersed in the dye solution may be room temperature, and may be, for example, 20-40° C., preferably 25-35° C., such as 20° C., 25° C., 30° C., 35° C., 40° C., etc., or other temperatures suitable for the combination of the polyionic film and the dye. Therefore, the polyionic film can be better combined with the dye in a proper time and temperature range, the property of the dye is not changed, and the obtained occult blood detection film has good performance and high efficiency.

In some embodiments, the preparation method for the polyionic film comprises the following steps:

providing a base plate assembly comprising a base plate and a first lubricant disposed on the base plate;

placing a film-forming solution of polyionic film on the base plate assembly, and putting a cover plate with a second lubricant on the film-forming solution, where the film-forming solution is in contact with the first lubricant and the second lubricant, respectively; and separating the polyionic film from the base plate assembly and the cover plate after a polymerization reaction of various raw materials in the film-forming solution to obtain the polyionic film.

In some embodiments, the base plate assembly further comprises a tinfoil, where the tinfoil is arranged on the base plate, and the first lubricant is arranged on the tinfoil. It should be understood that the base plate assembly may comprise a base plate, or may comprise a base plate and a tinfoil. When the base plate assembly comprises a tinfoil, the tinfoil needs to be flatly laid on the base plate, or the tinfoil flatly wraps the base plate, and then the first lubricant can be disposed on the tinfoil, which is more beneficial to the preparation of the polyionic film.

According to the preparation method for the polyionic film, by using the tinfoil and the lubricant, the film-forming solution before film formation is prevented from being directly contacted with the base plate or the cover plate, the integrity of the polyionic film and the thickness uniformity of the polyionic film are guaranteed, and the time required for separating the polyionic film can be greatly shortened. In addition, the method has the advantages of easy operation, short time, easy separation of products, uniform and adjustable film thickness.

Specifically, the base plate may be a glass plate, a stainless steel plate, a hard plastic plate resistant to ultraviolet light (ultraviolet light is not easily transmitted), or the like. Among these base plates, it is preferable that the base plate is a glass plate. The glass plate has the advantages of easily available raw materials and low cost. In addition, the glass plate has good heat resistance and is easy to cool after the polymerization reaction is generated by ultraviolet irradiation, so that the operation time is shortened.

Specifically, the cover plate may be a glass plate or a hard plastic plate or the like. Preferably, the cover plate may be a transparent glass plate or a transparent hard plastic plate. The transparent glass plate or the hard transparent hard plastic plate is used for enabling the polymerization reaction to be carried out under the irradiation of ultraviolet light, so that the reaction speed is accelerated, and an optional method is provided for carrying out the polymerization reaction.

Specifically, the lubricant used, such as the first lubricant or the second lubricant, needs to be inert to ultraviolet light and not interfere with ultraviolet light. The first lubricant and the second lubricant may be of the same type or different types.

In some embodiments, the first lubricant and the second lubricant are each independently selected from at least one of white petrolatum, silicone oil, paraffin, mineral oil, or grease. Exemplarily, the first lubricant may be white petrolatum, may be silicone oil, may be mineral oil, etc., and the second lubricant may be white petrolatum, may be silicone oil, may be grease, etc.

In the field of medical devices, the lubricant used needs to be non-toxic, corrosion-free, residue-free and transparent. Specifically, the fields with high requirements on safety, such as sensors and drug controlled release, have higher requirements on lubricants, and common medical-grade lubricants can be adopted.

Specifically, in the preparation method for the polyionic film, a film-forming solution can be prepared in advance. Then, the tinfoil is flatly laid on the base plate, or the tinfoil flatly wraps the base plate, or the tinfoil can be wiped with a lint-free cloth until the tinfoil has no wrinkles. The smooth surface of the tinfoil is put upward, then a first lubricant such as white petrolatum is smeared on the tinfoil, and the lint-free cloth is used to wipe until the surface is smooth. Then, the prepared film-forming solution is covered on the tinfoil with the first lubricant, and the tinfoil with the film-forming solution is covered with a cover plate which is pre-coated with the second lubricant. It can be understood that the upper and lower surfaces of the film-forming solution can be in contact with the second lubricant and the first lubricant, respectively.

Alternatively, the base plate may be wetted with a wetting solution before the tinfoil is laid on the base plate. The purpose of wetting the base plate is to remove air between the base plate and the tinfoil. In addition, the bonding force between the base plate and the tinfoil is increased through the adhesion of the wetting solution and the tinfoil, so that it is easier to flatten the tinfoil, and thereby improve the flatness of the surface of the tinfoil. There may be various wetting solutions for wetting the base plate, but the wetting solution is preferably water, ethyl alcohol, or a mixed solution thereof from the viewpoint of source, cost, and environmental protection.

In addition, in other embodiments, the base plate assembly may include only the base plate and the first lubricant. Specifically, in the preparation method for the polyionic film, a film-forming solution can be prepared in advance. Then, a first lubricant such as white petrolatum is coated on the base plate, and the first lubricant is wiped with a lint-free cloth until the surface is smooth. Then, the prepared film-forming solution is covered on the base plate with the first lubricant, and the cover plate coated with the second lubricant in advance is covered on the base plate carrying the film-forming solution. It can be understood that the upper and lower surfaces of the film-forming solution can be in contact with the second lubricant and the first lubricant, respectively.

Specifically, in some embodiments, the preparation method for the film-forming solution comprises:

uniformly mixing an ionic liquid monomer and a base film monomer, adding a cross-linking agent and an initiator, and then carrying out a second ultrasonic treatment to obtain the film-forming solution. Where the second ultrasonic treatment may be ultrasonic oscillation.

Preferably, the time of the second ultrasonic treatment is 10-30 min; typically but not limiting, for example, may be 10 min, 15 min, 20 min, 25 min, 30 min, etc.

Preferably, the preparation method for the film-forming solution further comprises performing a first ultrasonic treatment on the ionic liquid monomer, wherein the first ultrasonic treatment lasts for 10-30 min; typically but not limiting, for example, may be 10 min, 15 min, 20 min, 25 min, 30 min, etc. Wherein the first ultrasonic treatment may be ultrasonic oscillation.

In the preparation of the film-forming solution, compared with the existing "two-step method" for preparing the ionic liquid, the preparation method provided by the embodiments of the present application can obviously improve the preparation efficiency of the film-forming solution by using an ultrasonic method, greatly shorten the preparation time, and is easy to operate and good in controllability. Therefore, the preparation efficiency of the film-forming solution can be further improved by adopting the preparation method for the film-forming solution.

According to the embodiments of the present application, different film-forming solutions can be selected according to different requirements. The component of the ionic liquid in the film-forming solution may be one or more of an imidazole ionic liquid, a pyridine ionic liquid, a quaternary ammonium salt ionic liquid, a quaternary phosphine ionic liquid or a pyrrolidine ionic liquid, or may also be other types of ionic liquids well known in the art.

Preferably, the ionic liquid monomer comprises bromobutane and vinylimidazole.

Preferably, the base film monomer comprises acrylonitrile.

Preferably, the cross-linking agent comprises N,N'-methanediylbisprop-2-enamide (MBA).

Preferably, the initiator comprises 2,4,6-(trimethylbenzoyl) diphenyl phosphine oxide (TPO).

Specifically, in the preparation of the film-forming solution, the molar ratio of bromobutane to vinyl imidazole may be 2:1 to 1:1, which may be, for example, 1:1. To ensure complete reaction, the mass of the acrylonitrile needs to be greater than or equal to the sum of the mass of the bromobutane and vinylimidazole. In consideration of the reaction ratio, the conversion rate, the dosage and the subsequent cleaning treatment process of the three components, the mass of the acrylonitrile is preferably the sum of the mass of the bromobutane and the vinylimidazole. The mass of the cross-linking agent is 8 wt %-12 wt % of the total mass of the bromobutane, the vinylimidazole and the acrylonitrile, and may be, for example, 8 wt %, 9 wt %, 10 wt %, 12 wt %, etc. The mass of the initiator is 0.5 wt-2 wt % of the total mass of the bromobutane, the vinylimidazole and the acrylonitrile, and may be, for example, 0.5 wt %, 1 wt %, 1.5 wt %, 2 wt %, etc. It should be understood that the ratio of the above raw materials is not limited thereto, and can be appropriately adjusted according to the actual process conditions.

Specifically, the preparation of the film-forming solution may include the following steps: mixing the bromobutane and vinylimidazole in equal molar ratio, and carrying out an ultrasonic treatment on the obtained mixed solution for 15 min until the two are fully mixed; adding an amount of acrylonitrile equal to the total mass of the bromobutane and the vinylimidazole after removing impurities; then, adding MBA with a mass ratio of 8 wt % calculated by the total mass of the bromobutane, the vinylimidazole and the acrylonitrile, and TPO with a mass ratio of 1 wt % calculated by the total mass of the bromobutane, the vinylimidazole and the acrylonitrile, and after the addition, carrying out the ultrasonic treatment for 15 min to obtain a film-forming solution, wherein the obtained film-forming solution is a clear transparent solution. In this preparation step, the ultrasonic treatment can increase the energy field for the mixed solution of bromobutane and vinylimidazole, thus accelerating the reaction.

Further, in the preparation method for the occult blood detection film, raw materials in the film-forming solution are subjected to polymerization reaction, and in some embodiments, the polymerization reaction is carried out under the irradiation of ultraviolet light.

The wavelength of the ultraviolet light is preferably 250-400 nm, typically but not limiting, for example, may be 250 nm, 300 nm, 400 nm, etc.

The time of ultraviolet light irradiation is preferably 10-30 min, typically but not limiting, for example, may be 10 min, 20 min, 30 min, etc.

Alternatively, the polymerization reaction may be carried out under heating while being carried out under irradiation of ultraviolet light. Where, the heating temperature may be 20-60° C., and typically but not limiting, for example, may be 20° C., 30° C., 40° C., 50° C., 60° C., etc.

Polymerization reaction under this condition is conducive to obtaining the polyionic film with excellent performance and high efficiency.

The polymerization reaction may be initiated by an initiator. The initiator may be a common initiator in the art, such as photoinitiator 907, photoinitiator 184, azobisisobutyronitrile, benzoin and derivatives thereof, etc. Those skilled in the art may select an appropriate initiator according to the specific components of the film-forming solution.

Further, in the preparation method for the occult blood detection film, after the polymerization reaction of various raw materials in the film-forming solution, a separation is performed (for example, the polyionic film is separated from the cover plate). In some embodiments, the method of separation comprises: removing the base plate assembly, placing the cover plate attached with the polyionic film in a standing solution, standing for 10-30 min, and removing the cover plate to obtain the polyionic film; alternatively, removing the cover plate, placing the base plate assembly attached with the polyionic film in the standing solution, standing for 10-30 min, and removing the base plate assembly to obtain the polyionic film. The base plate assembly comprises the base plate.

Alternatively, in some other embodiments, when the base plate assembly comprises the base plate and the tinfoil, the method of separation comprises: removing the base plate, placing the cover plate and the tinfoil attached with the polyionic film in the standing solution, standing for 10-30 min, and removing the tinfoil to obtain the polyionic film.

Alternatively, the standing solution may be water or other solutions.

Therefore, by placing the cover plate or the base plate assembly attached with the polyionic film in the standing solution such as water, and then separating the polyionic film from the cover plate or the base plate in a standing mode, the automatic peeling of the polyionic film from the cover plate or the base plate is realized. In such a way, the polyionic film can be automatically separate from the cover plate or the base plate, which is simple in operation, while improving the yield rate and production efficiency.

Alternatively, the polyionic film obtained by separation is cleaned, for example, by ultrasonic cleaning in clean water, absolute ethanol and clean water in sequence.

It can be seen from the above that, according to the preparation method in the embodiments of the present application, through the use of the tinfoil, the first lubricant and the second lubricant, not only the integrity of the finished occult blood detection film and the uniformity and stability of the film thickness can be ensured, but also the polyionic film can be separated more easily. Specifically, the preparation method for the polyionic film provided by the present application realizes the automatic peeling of the polyionic film, and greatly shortens the time required for separation. Meanwhile, preparing the film-forming solution by ultrasonic method also greatly shortens the time of preparation, and the operation is simple and efficient. Therefore, compared with the existing preparation method, the preparation method for the polyionic film has the characteristics of easy operation, high efficiency, short time, etc.

In a third aspect, in some embodiments, an application of an occult blood detection film prepared by the preparation method for the occult blood detection film or of the occult blood detection film in occult blood detection is provided. The application comprises:

contacting the occult blood detection film with a sample to be detected, wherein the dye in the occult blood detection film reacts with hemoglobin, and the color of the occult blood detection film changes.

The occult blood detection film disclosed by the present application can be applied to occult blood detection, has the advantages of easiness and convenience in operation, strong anti-interference performance, obvious change before and after detection, high detection speed, high efficiency and the like, and can alleviate the defects of complex equipment, high technical requirements, complex detection, high cost and the like of the existing occult blood detection method.

For example, when the occult blood detection film is used for urine occult blood or fecal occult blood, a sample may be collected first (collection of the sample to be detected), for example, a urine sample or a fecal sample may be collected first. Then, the occult blood detection film is placed in a urine sample or a fecal sample, and the color change of the occult blood detection film is observed to determine whether there is fecal occult blood or urine occult blood or the approximate concentration range of the occult blood contained therein. The greater the difference of color change of the occult blood detection film before and after detection, the more hemoglobin in the detection sample; on the contrary, the less the difference of color change of the occult blood detection film before and after detection, the less hemoglobin in the detection sample. If the color of the detection film does not change, there is no occult blood in the urine or fecal sample. When occult blood is found in the sample, a pathological examination is recommended to determine the specific cause of occult blood.

In addition, in the detection process, the detection can be repeated for two or three times, the result is recorded in the form of taking images, and the average value is taken during subsequent analysis and processing, so that the accuracy of the detection result can be improved.

In some embodiments, the detection method further comprises: determining the concentration of hemoglobin according to different colors shown by the occult blood detection film, wherein the occult blood detection film has different colors in environments with hemoglobin concentrations.

For example, when the dye in the occult blood detection film is a methylene blue dye, the methylene blue dye can change from blue oxidized form to colorless or light yellow reduced form due to the effect of hemoglobin in an environment containing high concentration of hemoglobin. In an environment with a low concentration of hemoglobin, in which there is less hemoglobin, the methylene blue dye is blue or light blue. Therefore, after the detection, when the methylene blue dye is blue or light blue, it means that the concentration of hemoglobin in the environment (digestive tract, for example) is low, and when the methylene blue dye is colorless or light yellow, it means that the concentration of hemoglobin in the environment is high.

It should be understood that, for the same or similar parts in the application of the occult blood detection film according to the third aspect as the occult blood detection film and the preparation method according to the first and second aspects, reference may be made to the description of the occult blood detection film and the preparation method, which are not repeated here.

In a fourth aspect, in some embodiments, there is provided an occult blood detection kit comprising the aforementioned occult blood detection film.

As can be seen from the above, the occult blood detection kit according to the embodiments of the present application comprises the occult blood detection film, and thus has at least the same advantages as the occult blood detection film and the preparation method and application thereof, which are not described herein. The principle of the occult blood detection kit is mainly that the dye in the occult blood detection film reacts with the substance in the occult blood, such as hemoglobin, for color development, and when the hemoglobin concentration is different, the occult blood detection film has different colors, so that the hemoglobin concentration or whether the occult blood is contained can be determined by detecting the color change degree of the occult blood detection film before and after detection.

It should be understood that the kit can detect whether hemoglobin is contained in human stool, urine or other digestive tract environments through color change, the detection method is simple, the test speed is fast, the effect is obvious, and the kit can be used as an important detection test for detecting gastrointestinal bleeding or early screening of gastrointestinal malignant tumors.

In some embodiments, the occult blood detection kit further comprises a standard colorimetric card for occult blood detection, or a standard color scale for occult blood detection. Further, the occult blood detection kit may further comprise a housing (packaging box) and a user guide.

The occult blood detection kit may have a housing (packaging box), and an occult blood detection film and a standard colorimetric card may be placed in the housing, and a user guide or the like may also be placed therein. The number of the occult blood detection films may not be limited, for example, 3-5 occult blood detection films or more occult blood detection films can be contained.

According to an embodiment of the present application, when the occult blood detection kit is used for occult blood detection, the method comprises:

after the preparation of the occult blood detection film, the color of the occult blood detection film before detection can be recorded by taking images, or the occult blood detection film can be compared with standard colors on the kit and recorded;

then, the occult blood detection film is placed in the sample (blood) to be detected, and after several seconds, it can be observed that the color of the occult blood detection film slowly changes, for example, from blue to yellow. After the color is stable, the occult blood detection film is taken out, the color of the occult blood detection film after detection is recorded, and the color of the occult blood detection film after detection is compared with the color of the occult blood detection film before detection for analysis and judgment, or the color of the occult blood detection film can be compared with a color card number for verification, or can be compared with a standard color scale or a standard colorimetric card in the kit, and the change of color depth corresponds to different hemoglobin concentrations.

Where, the standard color scale or standard colorimetric card for occult blood detection can be prepared by the following method.

Prepare hemoglobin solutions of a range of concentrations, for example, 0 ug/mL, 0.7 ug/mL, 3.5 ug/mL, 1 ug/mL, 14 ug/mL, 28 ug/mL and 140 ug/mL.

Respectively taking the hemoglobin solutions with various concentrations, respectively placing them into colorimetric vessels, respectively adding the same occult blood detection films, standing for a certain period of time, and taking out the occult blood detection films after the color is stable. A camera is used to record the color development results of the occult blood detection films after detection, and after capturing images, the images with color gradient are used to form the standard color scale of occult blood or (through computer processing) printed to make the standard colorimetric card for occult blood detection.

In addition, if it is not sensitive to color, a color analysis software can be used to analyze the color of the occult blood detection film. For example, the color of the occult blood detection film can be analyzed by using MATLAB Software, and the color can be quantized using color space knowledge. Specifically, for example the method can use a HIS (Hue-Saturation-Intensity) color model, that is, use the H, S, I parameters to describe the color characteristics. Among them, H (Hue) defines the wavelength of color, namely hue, indicating the perception of different colors by human senses; S (Saturation) represents the depth of color and the purity of color, namely saturation. The greater the saturation, the brighter the color look; I (Intensity) represents intensity or brightness, corresponding to imaging brightness and image gray scale, which is the brightness of color. HSI model reflects the basic properties of human perception of color, and corresponds to the results of human perception of color one by one. Therefore, HIS model is widely used in image representation and processing system perceived by human visual system. In addition, RGB can be converted into HIS model, that is, the RGB color image and HIS model can be mutually converted as required, which are not described in detail. The relationship between the hemoglobin concentration and the color of the occult blood detection film is shown in FIG. 2.

It should be noted that the values in FIG. 2 may fluctuate to a certain extent due to the influence of factors such as environment, and the fluctuation range is ±5.

It can be seen from the data in FIG. 2 that there is a good linear relationship between saturation (S) value and hemoglobin concentration, specifically as shown in FIG. 1. As different colors have respective color value combinations, a standard colorimetric card or a substitute colorimetric card can be made according to the color value combinations, so that the mode can be selected to determine the corresponding hemoglobin concentration and the color of the occult blood detection film.

According to the embodiments of the present application, the most intuitive comparison mode can be adopted, that is, whether the occult blood is contained can be determined by detecting whether the color of the occult blood detection film changes before and after the detection. The relationship between saturation (S) value and hemoglobin concentration can also be used to quantify the occult blood situation. Other calculation methods or other values (other than the S value) may also be used for comparison to determine the hemoglobin concentration.

In order to facilitate the understanding of the present application, the present application can be further described in combination with specific examples below. In the following examples, the raw materials used are commercially available unless otherwise specified.

Embodiment 1

The preparation of the occult blood detection film comprises the following steps:

taking bromobutane and vinylimidazole in equal molar ratio, placing in a glass bottle, and performing ultrasonic oscillation for 15 min until the two are fully mixed. After removing impurities, adding an amount of acrylonitrile solution with the same mass as the bromobutane and the vinylimidazole, then adding MBA accounting for 8% of the total mass of the bromobutane, the vinylimidazole and the acrylonitrile and TPO accounting for 1% of the total mass of the bromobutane, the vinylimidazole and the acrylonitrile, and then performing ultrasonic oscillation for 15 min to form clear and transparent film-forming solution.

Preparing a glass plate (e.g. 10 cm*10 cm), wetting the glass plate with water, then sticking the tinfoil on the surface of the glass plate, with the smooth side of the tinfoil facing upward, wiping it with a lint-free cloth until there is no wrinkle, applying the first lubricant, white petrolatum, on the tinfoil, and continuing to wipe it with the lint-free cloth until the surface is smooth. Then, putting the film-forming solution on the tinfoil with white petrolatum, and then slowly pressing the glass cover plate with the contact surface uniformly coated with the second lubricant, white petrolatum.

Irradiating with 250 nm ultraviolet light for 15 min in a polymerization reaction chamber to make the film-forming solution undergo polymerization reaction to form a transparent film. After that, taking out the glass plate together with the tinfoil and cooling to room temperature. The transparent film can be found sticking to the glass cover plate. Placing the glass cover plate with the transparent film in water for 20 min, and the transparent film is automatically separated from the glass cover plate, and the complete transparent detection film floats on the water surface. Performing ultrasonic cleaning of the obtained film in clear water, absolute ethyl alcohol and clear water in sequence to obtain the polyionic film.

Immersing the 200 $mm^2$ polyionic film in a 2 mg/mL of methylene blue dye solution, taking it out after 30 min at room temperature and cleaning with clear water to obtain the occult blood detection film.

Embodiment 2

The preparation of the occult blood detection film is different from that of embodiment 1 only in that:

immersing the 200 $mm^2$ polyionic film in a 1 mg/mL of methylene blue dye solution, taking it out after 30 min at room temperature and cleaning with clear water to obtain the occult blood detection film.

Embodiment 3

The preparation of the occult blood detection film is different from that of embodiment 1 only in that:

immersing the 200 $mm^2$ polyionic film in a 2 mg/mL of procyanidin dye solution, taking it out after 30 min at room temperature and cleaning with clear water to obtain the occult blood detection film.

Embodiment 4

The preparation of the occult blood detection film comprises the following steps:

taking the bromobutane and vinylimidazole with a molar ratio of 2:1, placing in a glass bottle, and performing ultrasonic oscillation for 20 min until the two are fully mixed. After removing impurities, adding an amount of acrylonitrile with the same mass as the bromobutane and the vinylimidazole, then adding MBA accounting for 9% of the total mass of the bromobutane, the vinylimidazole and the acrylonitrile and TPO accounting for 1.5% of the total mass of the bromobutane, the vinylimidazole and the acrylonitrile, and then performing ultrasonic oscillation for 15 min to form clear and transparent film-forming solution.

Preparing a glass plate (e.g. 10 cm*10 cm glass plate), wetting the glass plate with water, then sticking the tinfoil on the surface of the glass plate, with the smooth side of the tinfoil facing upward, wiping it with a lint-free cloth until there is no wrinkle, applying the first lubricant, white petrolatum, on the tinfoil, and continuing to wipe it with the lint-free cloth until the surface is smooth. Then, putting the film-forming solution on the tinfoil with white petrolatum, and then slowly pressing the glass cover plate with the contact surface uniformly coated with the second lubricant, white petrolatum.

Irradiating with 265 nm ultraviolet light for 15 min in a polymerization reaction chamber to make the film-forming solution undergo polymerization reaction to form a transparent film. After that, taking out the glass plate together with the tinfoil and cooling to room temperature. The transparent film can be found sticking to the glass cover plate. The glass cover plate with the transparent film can be placed in water for 20 min, then the transparent film is automatically separated from the glass cover plate, and the complete transparent detection film floats on the water surface. Performing ultrasonic cleaning of the obtained film in clear water, absolute ethyl alcohol and clear water in sequence to obtain the polyionic film.

Immersing the 200 $mm^2$ polyionic film in a 2 mg/mL of methylene blue dye solution, taking it out after 25 min at room temperature and cleaning with clear water to obtain the occult blood detection film.

Embodiment 5

The preparation of the occult blood detection film comprises the following steps:

taking the bromobutane and vinylimidazole with a molar ratio of 1.5:1, placing in a glass bottle, and performing ultrasonic oscillation for 30 min until the two are fully mixed. After removing impurities, adding an amount of acrylonitrile with the same mass as the bromobutane and vinylimidazole, then adding MBA accounting for 12% of the total mass of the bromobutane, the vinylimidazole and the acrylonitrile and TPO accounting for 2% of the total mass of the bromobutane, the vinylimidazole and the acrylonitrile, and then performing ultrasonic oscillation for 25 min to form clear and transparent film-forming solution.

Preparing a glass plate (e.g. 10 cm*10 cm), wetting the glass plate with water, then sticking the tinfoil on the surface of the glass plate, with the smooth side of the tinfoil facing upward, wiping it with a lint-free cloth until there is no wrinkle, applying the first lubricant, silicone oil, on the tinfoil, and continuing to wipe it with the lint-free cloth until the surface is smooth. Then, putting the film-forming solution on the tinfoil with silicone oil, and then slowly pressing the glass cover plate with the contact surface uniformly coated with the second lubricant, white petrolatum.

Then, irradiating with 300 nm ultraviolet light for 20 min in a polymerization reaction chamber to make the film-forming solution undergo polymerization reaction to form a transparent film. After that, taking out the glass plate together with the tinfoil and cooling to room temperature. The transparent film can be found sticking to the glass cover plate. The glass cover plate with the transparent film can be placed in water for 20 min, the transparent film is automatically separated from the glass cover plate, and the complete transparent detection film floats on the water surface. Performing ultrasonic cleaning of the obtained film in clear water, absolute ethyl alcohol and clear water in sequence to obtain the polyionic film.

Immersing the 500 $mm^2$ polyionic film in a 4 mg/mL of procyanidin dye solution, taking it out after 40 min at room temperature and cleaning with clear water to obtain the occult blood detection film.

Embodiment 6

The preparation of the occult blood detection film comprises the following steps:

Taking the bromobutane and vinylimidazole with a molar ratio of 1:1, placing in a glass bottle, and performing ultrasonic oscillation for 15 min until the two are fully mixed. After removing impurities, adding an amount of acrylonitrile with 1.2 times the mass as the bromobutane and the vinylimidazole, then adding MBA accounting for 10% of the total mass of the bromobutane, the vinylimidazole and the acrylonitrile and TPO accounting for 1.5% of the total mass of the bromobutane, the vinylimidazole and the acrylonitrile, and then performing ultrasonic oscillation for 20 min to form clear and transparent film-forming solution.

Preparing a smooth stainless steel plate, wetting the stainless steel plate with water, attaching the tinfoil to the surface of the stainless steel plate with the smooth surface of the tinfoil facing upward, wiping the tinfoil with a lint-free cloth until there is no wrinkle, applying the first lubricant, grease, on the tinfoil, and continuing to wipe the tinfoil with the lint-free cloth until the surface is smooth. Then, putting the film-forming solution on the tinfoil with grease, and then slowly pressing the glass cover plate with the contact surface uniformly coated with the second lubricant, white petrolatum.

Then, irradiating with 250 nm ultraviolet light for 15 min in a polymerization reaction chamber to make the film-forming solution undergo polymerization reaction to form a transparent film. Then, taking out the stainless steel plate together with the tinfoil and cooling it to room temperature. The transparent film can be found sticking to the glass cover plate. Placing the glass cover plate with the transparent film in water for 20 min, and the transparent film is automatically separated from the glass cover plate, and the complete transparent detection film floats on the water surface. Performing ultrasonic cleaning of the obtained film in clear water, absolute ethyl alcohol and clear water in sequence to obtain the polyionic film.

Immersing the 500 $mm^2$ polyionic film in a 4 mg/mL of methylene blue dye solution, taking it out after 20 min at room temperature and cleaning with clear water to obtain the occult blood detection film.

Application Embodiment 1

Fecal Occult Blood Test:

cutting the occult blood detection film prepared in embodiment 1 (or other examples) into pieces and then the detection film pieces can be directly placed in the urinal or different areas of the toilet to observe color changes. After the color is stable, the detection film can be taken out. If the color of the detection film changes from blue to yellow, it indicates the existence of occult blood, and can be compared with the standard colorimetric card for occult blood detection in the detection kit, so as to determine the hemoglobin concentration.

Compared with the traditional method of "fecal occult blood detection test strip", after each defecation, a fecal collection stick is used for multi-point sampling in the feces, then a special fecal sample diluent is used for dissolving, after dissolution, a few drops of suspension are dripped into a designated reaction container for reaction, and after 5 minutes, the reaction result can be observed. The occult blood detection method of the application embodiment is more convenient and fast, is easy to operate and is fast to detect.

The person skilled in the art realizes that the present invention by no means is limited to the preferred embodiments described above. On the contrary, many modifications and variations are possible within the scope of the appended claims. Any modifications, equivalent substitutions, improvements, etc. made within the spirit and principles of this disclosure are intended to be included within the scope of the present invention.

It should be noted that a part of this patent application document contains contents protected by copyright. The copyright holder retains the copyright, except for making copies of patent documents or the contents of recorded patent documents at the Patent Office.

The invention claimed is:

1. A preparation method for an occult blood detection film, which is for occult blood detection, the method comprising the following steps:

providing a base plate assembly comprising a base plate and a first lubricant disposed on the base plate;

placing a film-forming solution of a polyionic film on the base plate assembly, and putting a cover plate with a second lubricant on the film-forming solution, wherein the film-forming solution is in contact with the first lubricant and the second lubricant, respectively;

and separating the polyionic film from the base plate assembly and the cover plate after a polymerization reaction of various raw materials in the film-forming solution to obtain the polyionic film;

immersing the polyionic film in a dye solution and making a dye attached to the polyionic film to obtain an occult blood detection film; wherein the dye reacts with hemoglobin, and the color of the dye is different in environments with different hemoglobin concentrations, and the dye comprises at least one of a methylene blue dye or a procyanidin dye.

2. The preparation method of claim 1, wherein the concentration of the dye in the dye solution is 0.5-5 mg/mL, or 1-2 mg/mL.

3. The preparation method of claim 1, wherein the time for immersing the polyionic film into the dye solution is 20-40 min, or 25-30 min and the temperature for immersing the polyionic film in the dye solution is 20-40° C., or 25-35° C.

4. The preparation method of claim 1, wherein the base plate assembly further comprises a tinfoil, wherein the tinfoil is arranged on the base plate, and the first lubricant is arranged on the tinfoil.

5. The preparation method of claim 1, wherein the first lubricant and the second lubricant are each independently selected from at least one of white petrolatum, silicone oil, paraffin, mineral oil, or grease.

6. The preparation method of claim 1, wherein the polymerization reaction is carried out under the irradiation of ultraviolet light;

the wavelength of the ultraviolet light is 250-400 nm;

and the irradiation time of the ultraviolet light is 10-30 min.

7. The preparation method of claim 1, wherein the method of separating the polyionic film from the base plate assembly and the cover plate comprises:

removing the base plate assembly, placing the cover plate attached with the polyionic film in a standing solution, standing for 10-30 min, and removing the cover plate to obtain the polyionic film; or, removing the cover plate, placing the base plate assembly attached with the polyionic film in a standing solution, standing for 10-30 min, and removing the base plate assembly to obtain the polyionic film; or, removing the base plate, placing the cover plate attached with the polyionic film and the base plate in a standing solution, standing for 10-30 min, and removing the base plate to obtain the polyionic film.

8. The preparation method of claim 7, wherein after separating the polyionic film from the base plate assembly and the cover plate, the method further comprises the step of cleaning the polyionic film, comprising ultrasonic cleaning in clear water, an alcohol solution and clear water in sequence.

9. The preparation method of claim 1, wherein the preparation method for the film-forming solution comprises:

uniformly mixing an ionic liquid monomer and a base film monomer, adding a cross-linking agent and an initiator, and then carrying out a second ultrasonic treatment to obtain the film-forming solution; and the time of the second ultrasonic treatment is 10-30 min.

10. The preparation method of claim 9, wherein the preparation method for the film-forming solution further comprises performing a first ultrasonic treatment on the ionic liquid monomer, wherein the first ultrasonic treatment lasts for 10-30 min.

11. The preparation method of claim 9, wherein the film-forming solution comprises at least one of an imidazole ionic liquid, a pyridine ionic liquid, a quaternary ammonium salt ionic liquid, a quaternary phosphine ionic liquid or a pyrrolidine ionic liquid;

or, the ionic liquid monomer comprises bromobutane and vinylimidazole, or a molar ratio of the bromobutane to the vinylimidazole is 2:1 to 1:1;

or, the base film monomer comprises acrylonitrile; or the mass of the acrylonitrile is greater than or equal to the sum of the mass of the bromobutane and vinylimidazole;

or, the cross-linking agent comprises N,N'-methanediylbisprop-2-enamide; or the mass of the cross-linking agent is 8 wt %-12 wt % of the total mass of the bromobutane, the vinylimidazole and the acrylonitrile;

or, the initiator comprises 2,4,6-(trimethylbenzoyl) diphenyl phosphine oxide; or the mass of the initiator is 1 wt %-4 wt % of the total mass of the bromobutane, the vinylimidazole and the acrylonitrile.

12. An occult blood detection film, wherein the film is prepared by the preparation method for the occult blood detection film of claim 1.

13. A method of using a detection film, comprising providing an occult blood detection film of claim 12;

contacting the occult blood detection film with a sample to be detected, wherein the dye in the occult blood detection film reacts with hemoglobin, and the color of the occult blood detection film changes.

14. The method of claim 13, further comprising:

determining the concentration of the hemoglobin according to different colors shown by the occult blood detection film, wherein the occult blood detection film has different colors in environments with different hemoglobin concentrations.

* * * * *